United States Patent [19]
Yamanouchi et al.

[11] Patent Number: 5,288,706
[45] Date of Patent: Feb. 22, 1994

[54] MEDICAMENT FOR PREVENTION AND REMEDY OF DISEASES OF THE PANCREAS AND OTHERS

[75] Inventors: Toshikazu Yamanouchi, Tokyo; Akira Awaya, Yokohama; Hisashi Kobayashi, Mobara; Yusaku Ishizuka, Yokohama; Hayao Abe, Mobara, all of Japan

[73] Assignee: Mitsui Toatsu Chemicals, Incorporated, Tokyo, Japan

[21] Appl. No.: 19,347

[22] PCT Filed: Dec. 23, 1988

[86] PCT No.: PCT/JP88/01317
    § 371 Date: Aug. 18, 1989
    § 102(e) Date: Aug. 18, 1989

[87] PCT Pub. No.: WO89/06136
    PCT Pub. Date: Jul. 13, 1989

Related U.S. Application Data

[63] Continuation of Ser. No. 702,117, May 16, 1991, abandoned, which is a continuation of Ser. No. 397,498, Aug. 18, 1989, abandoned.

[30] Foreign Application Priority Data

Dec. 25, 1987 [JP] Japan ................. 62-327180

[51] Int. Cl.$^5$ ................. A61K 37/02; C07K 7/06
[52] U.S. Cl. ................. 514/15; 514/866
[58] Field of Search ................. 514/15, 866

[56] References Cited

U.S. PATENT DOCUMENTS

| | | | |
|---|---|---|---|
| 4,098,777 | 7/1978 | Veber et al. | 530/328 |
| 4,229,438 | 10/1980 | Fujino et al. | 514/15 |
| 4,301,065 | 11/1981 | Bach et al. | 530/328 |
| 4,680,276 | 7/1987 | Bach et al. | 530/328 |

FOREIGN PATENT DOCUMENTS 54-148722 11/1979 Japan .
58-52225 3/1983 Japan .
2109684A 3/1983 United Kingdom .

OTHER PUBLICATIONS

Anatomical Record, 109, p. 377, 1951.
Clinics in Immunology and Allergy, 3(1), p. 133, 1983.
Kolb et al., Diabetes Research, vol. 6, No. 1, pp. 21–27, 1987.
Fabris et al, Cellular Immunology, vol. 91, No. 2, pp. 325–335, 1985.

*Primary Examiner*—Lester L. Lee
*Attorney, Agent, or Firm*—Nixon & Vanderhye

[57] ABSTRACT

A medicament for prevention and remedy of diseases of pancreas and others is disclosed, which is characterized by containing as an effective ingredient thereof a nonapeptide having the following amino acid configuration:

pGlu-Ala-Lys-Ser-Gln-Gly-Gly-Ser-Asn or an ester and amide at the carboxyl group of the C-terminal of the asparagine or a pharmacologically acceptable salt thereof.

6 Claims, 1 Drawing Sheet

MEDICAMENT FOR PREVENTION AND REMEDY OF DISEASES OF THE PANCREAS AND OTHERS

This is a continuation of application Ser. No. 07/702,117, filed May 16, 1991 and now abandoned which is a continuation of Ser. No. 07/397,498 filed Aug. 18, 1989, now abandoned.

INDUSTRIAL APPLICABILITY

The present invention relates to a new medicament and a veterinary medicament. More particularly, the present invention relates to a medicament possessing hypoglycemic activity, insulitis blocking activity, anti-obese activity and anti-adiposis activity and being utilized for prevention and remedy of various types of diabetes, acute pancreatitis, chronic pancreatitis, corpulence, hyperlipidemia, diapetic neuropathy and atheromatous arteriosclerosis as well as a new medicament for prevention and remedy of gastritis, constipation, infected gastrointestinal canal, meteorismus, irritable colon syndrome, caries, hepatitis, diseases such as nephritis, and diseases of adrenal gland.

BACKGROUND ART

In Europe, America and Japan, the age of the population is now being older so that the number of patients suffering from adult diseases is increased. Diabetes is known as one of such adult diseases, which is classified into insulin dependent diabetes mellitus (referred to hereinafter as IDDM) and non-insulin dependent diabetes mellitus (referred to hereinafter as NIDDM).

It is known that IDDM chiefly attacks people of younger ages and that people of 18 years old are attacked by IDDM in Europe and America at a rate as high as 1/300-500 persons. The majority of diabetes patients are compelled to receive injection of insulin over their life span, thus raising many problems personally and socially.

Diabetes incurs various metabolic disordered based on the metabolic disorder of insulin and sugar and causes disorder in blood vessels and nervous system, thus being regarded as a terrible sickness attacking almost all organs in living body. Accordingly, an effective method for the remedy of diabetes is rapidly demanded.

At present, an insulin treatment or oral anti-diabetes drugs such as sulfonylurea preparations and biguanide preparations are used widely as a means for the remedy of diabetes. However, all of these preparations only serves to reduce the level of blood sugar allopathically but fail to become medicaments for completely curing diabetes.

In connection with the cause and factor of diabetes, there are a number of unsolved problems, but hereditary background and environmental factor are also regarded to be important. The infection of virus and some chemical substances are known as the environmental factor. A detailed contract mechanism of these is not yet known but autoimmunity mechanism to Langerhans islands is thought to be a cause of the attack.

Pancreatitis involving acute and chronic pancreatitis accompanying necrosis is a disease which may incur death if left without any treatment. In recent years, gabexate mesylate preparations are applied to this disease.

The present inventors have contemplated to develop a new type medicament which can be expected to be effective for complete remedy of diabetes and acute pancreatitis and for reducing these symptoms.

DISCLOSURE OF THE INVENTION

The present inventors have made extensive researches for finding such medicament in various peptides of natural origin which are of high safety.

As a result of the researches, it has been found for the first time that a nonapeptide known as the factor of thymic serum (FTS: Facteur thymique serique) and derivatives or salts thereof are effective to inhibit increase in the level of blood sugar of rats to which alloxan or streptozotosine has been administered. The present invention has been accomplished on the basis of the above finding and provides a medicament for prevention and remedy of various diseases including diabetes which contains the above nonapeptide or a derivative thereof as an effective ingredient.

One of the present inventors previously found that FTS was suitable as a therapeutic agent for multiple sclerosis, Guillain-Barre syndrome, inflammatory neuritis, polyneuritis and other various diseases accompanying immunodeficiency such as immunological demyelinating diseases, and provided such therapeutic agents (Japanese Laid-open Patent Appln. No. Sho. 58-52225). The fact that a nonapeptide known as FTS exhibits a preventive and therapeutic effects to various diseases including diabetes is quite unexpected from the prior art and was discovered for the first time by the present inventors.

In accordance with the present invention, there is provided a medicament for prevention and remedy of diseases such as diabetes, pancreatitis, etc., characterized by containing as an effective ingredient thereof a nonapeptide having the following amino acid configuration:

pGlu-Ala-Lys-Ser-Gln-Gly-Gly-Ser-Asn or an ester at the carboxyl group of the C-terminal of the asparagine or a pharmacologically acceptable salt thereof.

The nonapeptide used in the present invention can be prepared without difficulty according to a liquid phase or solid phase peptide synthetic method conventionally employed for the synthesis of usual peptides (Concerning these methods, please refer to Japanese Laid-open Patent Appln. No. Sho. 54-16425 and U.S. Pat. No. 4,301,065). Alternatively, the nonapeptide can be prepared also by a genotechnological or cell technological procedure.

The esters at the carboxyl group of C-terminal of the asparagine in the nonapeptide used in the present invention are those of the carboxylic acid pharmacologically acceptable and examples of such esters include methyl ester, ethyl ester, propyl ester, isopropyl ester, n-butyl ester, isobutyl ester, tert-butyl ester, n-pentyl ester, isopentyl ester, neopentyl ester, tert-pentyl ester, n-hexyl ester, sec-hexyl ester, heptyl ester, octyl ester, sec-octyl ester, tert-octyl ester, nonyl ester, decyl ester, undecyl ester, dodecyl ester, tridecyl ester, tetradecyl ester, hexdecyl ester, octadecyl ester, nonadecyl ester, eicocyl ester, cyclopentyl ester, cyclohexyl ester, cycloheptyl ester, cyclooctyl ester, allyl ester, isopropenyl ester, benzyl ester, o-, m- or p-chlorobenzyl ester, o-, m- or p-fluorobenzyl ester, o-, m- or p-boromobenzyl ester, o-, m- or p-iodobenzyl, o-, m- or p-methylbenzyl ester, o-, m- or p-ethylbenzyl ester, o-, m- or p-isopropylbenzyl ester, cinnamyl ester, aminoethyl ester, o-, m- or p-aminobenzyl ester, o-, m- or p-nitrobenzyl ester, o-, m- or p-methoxybenzyl ester, o-, m- or p-ethoxybenzyl ester, o-, m- or p-aminophenetyl ester, α-furfuryl ester, αthienylmethyl ester, α-pyridylmethyl ester, α-pyridylethyl ester, piperidinomethyl ester, α-piperidylmethyl ester, morpholinomethyl ester, α-morpholinylmethyl ester. The amides at the carboxyl group of C-terminal of the asparagine in the nonapeptide used in the present invention are those of carboxylic acid pharmacologically acceptable and examples of such amides include amide itself, methylamide, ethylamide, propylamide, isopropylamide, n-butylamide, isobutylamide, tert-butylamide, n-pentylamide, isopentylamide, neopentylamide, tert-pentylamide, n-hexylamide, sec-hexylamide, heptylamide, octylamide, sec-octylamide, tert-octylamide, nonylamide, decylamide, undecylamide, dodecylamide, tridecylamide, tetradecylamide, hexadecylamide, octadecylamide, nonadecylamide, eicosylamide, cyclopentylamide, cyclohexylamide, cycloheptylamide, cyclooctylamide, allylamide, isopropenylamide, benzylamide, o-, m- or p-chlorobenzylamide, o-, m- or p-fluorobenzylamide, o-, m- or p-bromobenzylamide, o-, m- or p-iodobenzylamide, o-, m- or p-methylbenzylamide, o-, m- or p-ethylbenzylamide, o-, m- or p-isopropylbenzylamide, cinnamylamide, aminoethylamide, o-, m- or p-aminobenzylamide, o-, m- or p-nitrobenzylamide, o-, m- or p-methoxybenzylamide, o-, m- or p-ethoxybenzylamide, o-, m- or p-aminophenethylamide, α-furfurylamide, α-thienylmethylamide, α-pyridylmethylamide, α-pyridylethylamide, piperidinomethylamide, α-piperidylmethylamide, morpholinoethylamide, α-morpholinylmethylamide, methoxycarbonyl-(α-mercapto-methyl)methylamide and ethoxycarbonyl-(α-mercapto-methyl)methylamide.

The above mentioned pharmacologically acceptable salts include acid-additions salts at the amino group of the nonapeptide and salts with bases at the carboxylic acid of the nonapeptide. The acid-addition salts include those with organic acids and inorganic acids. Illustrative of these salts are, for example, salts with carboxylic acids such as formic acid, acetic acid, propionic acid, trifluoroaetic acid, tartaric acid, fumaric acid, malic acid, maleic acid, oxalic acid and naphthoic acid and salts with sulfonic acids such as methanesulfonic acid, p-toluenesulfonic acid and naphthalenesulfonic acid as well as salts with inorganic acids such as hydrochloric acid, sulfuric acid, nitric acid and phosphoric acid.

The above mentioned salts with bases include salts with inorganic bases, such as alkali metal salts, alkaline earth metal salts and ammonium salts as well as salts with organic bases, i.e. salts with amines. Illustrative of these salts are lithium salt, sodium salt, potassium salt, calcium salt, ammonium salt, triethyl amine salt, ethanolamine salt, tris salt and dicyclohexylamine salt.

The medicament concerned with the present invention for prevention and remedy of diseases such as diabetes, pancreatitis, etc. can be prepared in a usual conventional pharmaceutical manner according to the type of the medicaments. An effective ingredient selected from the nonapeptide (referred to hereinafter simply as FTS), an ester, an amide and a salt thereof is processed properly with a pharmacologically acceptable carrier, excipient or diluent to a suitable type of medicament. The medicament can be made in any of the various types suitable for the route of administration such as external application, oral administration, non-oral administration, etc.

The effect of the preventive and therapeutic medicament of the present invention is confined by the experiments as described below. After allowing rats to fast for 24 hours, the rats were intravenously injected at their tail vain with alloxane (prepared by Kanto) or streptozotosine (referred to hereinafter as STZ: prepared by Sigma) and simultaneously with a given amount of the above mentioned FTS (one time administration) under anesthesia. With the lapse of time, blood was periodically extracted from a jugular vein of the rats to measure the blood sugar (glucose) value and blood plasma anhydroglucitol (referred to hereinafter as AG) value. Further, urine was consecutively collected from a urinary bladder and, after its retention for a given period of time, urinary sugar was measured as a total amount of urinary sugar (referred to hereinafter as US). As the US value is well reflected in the AG value in such relation that the AG value is decreased if the US value is great but the AG value is increased if the US value is small, the AG value is in fact a good index especially in case the US value is not obtained exactly according to a technical error in experiments. (T. Yamanouchi et al.; Diabetes 35, 204–209, 1986).

Typical results are shown in Tables 1, 2, 3 and 4 given hereinafter. As shown in Tables 1 and 2, it was observed that concerning the blood sugar value at every hour up to 7 hours of a group of the rats to which FTS had been administered, increase in the level of blood sugar in an acute phase was distinctly inhibited as compared with a control group, irrespective of alloxan-induced diabetes rats or STZ-induced diabetes rats. As shown in Table 4, it is noted that in case of the alloxan-induced diabetes rats to which FTS had been administered subcutaneously 20 hours and 44 hours after the initial administration of the nonapeptide (repetitive administration), increase in the level of blood sugar in a subacute phase after 71 hours was distinctly inhibited as compared with a control group. In case the rats were first injected intravenously with an inducer of sugar urine and then with FTS after one hour, inhibition to increase in the level of blood sugar at every hour was observed.

As shown in Table 3, it is noted in both types of diabetes rats that the US value was as high as about 150 mg and the AG value was decreased down to about 2 μg in control groups, while the US value was smaller and decrease in the AG value was correspondingly smaller in the group to which FTS had been administered. In case of repetitive administration of FTS in Table 4, it is also noted that the AG value was higher as compared with that in control group. In view of the foregoing, it is considered to be evident that FTS inhibits occurrence of the state of high level in blood sugar, or in other words, possesses an inhibitory action to occurrence of diabetes.

In case of changing the route of administering FTS to subcutaneous, intramuscular or intraperitoneal injection, increase in the levels of blood sugar and urinary sugar are also inhibited as in the above mentioned cases.

Further, FTS was administered to mice and rats with naturally occurring diabetes or hereditary diabetes. When NOD mice or BB rats known as model animals for diabetes type I or KK mice famous as animals with naturally occurring diabetes was injected intravenously, subcutaneously, intramuscularly or intraperiotoneally with FTS 1-3 times a week from the stage of 1-2 months after birth, inhibition or considerable delay of the occurrence of diabetes was observed. This was proved not only by blood biochemical data, the number of leucocytes and change in lymphocyte subset but according to a histopathological observation of pancreas.

In the experiments for BB rats using 7 rats as a control group and 7 rats as an FTS-administered group, a phosphate-buffered saline (PBS) was administered to the control group intraperitoneally once a week, while FTS-dissolved PBS was administered in a dose of 500 μg/kg to the FTS-administered group, and the body weight of the rats were measured once a week. After about 10 weeks old, the gain in body weight of the control group began to decrease and finally the body weight was reduced after further lapse of time. Contrary to this, the body weight of the FTS-administered group showed an increasing curve similar to that of the normal rats. A result of the experiments is shown in FIG. 1. Judging from the AG value in blood, the final rate of occurrence of diabetes was 6/7 (86%) in case of the control group and 2/7 (29%) in case of the FTS-administered group, thus showing a significant inhibitory effect to occurrence of diabetes. Even in case of occurrence of diabetes in the FTS-administered group, the symptom was weak as compared with the case of the control group, and the occurrence of diabetes tended to delay.

These results reveal that FTS is useful not only as a mere agent for lowering the level of blood sugar but also as a completely curing agent or a medicament for prevention of diabetes. The effect is obviously displayed by the administration of FTS alone, but it is possible to use insulin, an oral drug for diabetes jointly with FTS.

In researches made for checking the effect of FTS on dog models suffering from acute or chronic pancreatitis, it has been made clear that the pancreatitis is gradually cured by a blood biochemical test and a histopathological test. Thus, FTS is considered to be useful as a valuable medicament for the prevention and remedy of pancreatitis and as a desirable medicament in the point that FTS can prevent and cure diabetes accompanied with pancreatitis.

From other experiments, it has also been made clear that FTS is expected to have an effect as a new medicament for prevention and remedy of diseases or disorders such as corpulence, hyperlipidemia, atheromatous arteriosclerosis, diabetic and alcoholic neuropathy, etc. as well as a medicament for prevention and remedy of diseases or disorders such as gastritis, constipation, infected gastrointestinal canal, meteorismus, irritable colon syndrome, caries, hepatitis, nephritis and of disorder of adrenal glands etc.

To check any toxicity of the effective ingredient of the medicament of this invention, 100 mg/g of the effective ingredient was subcutaneously administered every day for consecutive 14 days to mice whereupon no abnormal symptom as found by external check. Further, 30 mg/kg of the effective ingredient was subcutaneously administered every day to rats for consecutive 21 days whereupon no abnormal symptom was found in external behavior observation and biochemical diagnosis of sera and in a result of pathological anatomy. Thus, the medicament of the present invention is a safe medicament of extremely low toxicity and can be administered for a long period of time.

As animals to which the medicament of this invention can be administered, there can be mentioned, for example, human, domestic animals such as cattle, horse, pig, sheep, goat, rabbit, dog and cat, mammalia kept in zoo or the like such as lion, elephant, giraffe, bear, gorilla, monkey and chimpanzee, various test animals such as mouse, rat, guinea pig and the like, domestic fowls such as fowl, and pets such as birds, reptiles, amphibia and fishes. The dose of the medicament is usually 0.1 μg-500 mg/day for 1 kg body weight of these animals. The medicament in these doses may be administered, for example, in 1–6 portions in a day. The dose may properly be increased or decreased according to ages, symptoms, etc. of the objects to be administered. No limitation exists in the route of administration of the medicament, but it may be administered by intravenous, intramuscular intracutaneous, subcutaneous and intrarectum injection. The medicament can be processed to an ointment which is applied to eyes, oral cavity, nasal cavity and skin. The medicament can be administered in the form of a suppository, a jelly, eye drops, nasal drops, preparations absorbable in nasal or oral cavity, an aerosol, a spray and oral preparations. In order to prevent the effective ingredient from rapid decomposition or inactivation in the living body, the effective ingredient may be processed with appropriate pharmaceutical ingredients, for example, alcoholic, oily or fatty physiologically harmless solid or liquid materials such as lecithin or a suspension liposome thereof to medical preparations in which the activity is maintained for a long period of time.

The medicament of the present invention can be administered together with other medicines, for example, various anti-diabetes agents, pancreatitis-curing agent, anti-obese agents, lipid level lowering agents, anti-arteriosclerosis agents, medicaments for peripheral nervous diseases, anti-hepatitis agents, anti-nephritis agents or biological response modifiers such as immunity-recovering agents, or alternatively may be incorporated with these as a combination agent to enhance clinical effects.

The present invention will now be illustrated in more detail by way of examples and experimental examples, but the present invention is not limited by these examples.

Example 1 A vial preparation for injection

In a distilled water was dissolved 1 mg of FTS.CH$_3$COOH.2H$_2$O (prepared by Mitsui Seiyaku Kogyo K K) and the solution was subjected to sterilizing filtration, charged into a vial and then subjected to lyophilization.

Example 2 An ampoule preparation for injection

In physical saline was dissolved 5 mg of FTS.CH$_3$COOH.2H$_2$O prepared by Mitsui Seiyaku Kogyo K K) and the solution was subjected to sterilizing filtration and charged into an ampoule.

Example 3 An injection preparation for subcutaneous injection

In a 2% carboxymethylcellulose PBS (physiological saline buffered with a phosphate) was suspended 2 mg per unit dose of FTS.CH$_3$COOH.2H$_2$O (prepared by Mitsui Seiyaku Kogyo K K). The suspension was mixed with Lipomal comprising soybean phosphatide (prepared by Huhtamaki OY/Leiras Pharmaceuticals Co.) or Intralipid (prepared by Cutter Laboratories) as an oil-in-water type emulsion for intravenous injection. In case of using Lipomal, the PBS solution dissolving FTS was mixed with an equiamount of Lipomal. In case of using Intralipid, 2.5 ml of the PBS solution dissolving FTS was mixed with 0.1 ml of Tween 80 (prepared by Sigma Chemicals Inc.) and 4.6 ml of Intralipid.

Example 4 A liposome preparation

There are 3 kinds of liposome preparations which are different in electric charge from one another. The liposome preparations are classified by their structures into 4 kinds.

There are 3 kinds of electric charge: neutral, positive and negative. In view of the structure, there are known 4 kinds; a multilaminar liposome (MLV, multilamellar vehicle), a small unilaminar liposome (SUV, small unilamellar vesicle), a large unilaminar liposome (LUV, large unilamellar vesicle), and one having a structure similar to LUV but having several lamellae (REV, reverse-phase evaporation vesicle).

(1) A neutral electric charge liposome enclosing FTS:

A phospholipid such as phosphatidylcholine or sphingomyelin and a solution of cholesterol in chloroform were mixed in a mole ratio of 2:1, 4:1 or 1:1 and the solvent was once removed from the mixture by distillation under reduced pressure. A solution of 1/100–1/1000 equivalent of FTS in PBS (physiological saline buffered with a phosphate) was added to the mixture and the whole was well mixed by the aid of a Vortex mixer whereby MLV was obtained.

This was then subjected to an ultrasonic treatment above a phase transition temperature (Tc) of the phospholipid whereby SUV was obtained.

An aqueous solution of calcium chloride was added to the resultant SUV and the mixture was incubated for 1 hour at 37° C. to effect hybridization. EDTA was then added and the mixture was incubated for 30 minutes at 37° C. to eliminate $Ca^{++}$ whereby LUV was obtained.

The method for preparing REV is as follows: After removing the solvent from a chloroform solution of the lipid by distillation under reduced pressure, a proper amount of diethyl ether is added to dissolve the lipid satisfactorily. A PBS solution of FTS is added to the solution and the mixture is subjected to an ultrasonic treatment to obtain a homogeneous uniphase solution. After concentrating the resultant solution under reduced pressure at room temperature, the PBS solution is added to the residue and the mixture was mixed well by the aid of a Vortex mixer to obtain REV.

(2) A positively charged liposome enclosing FTS:

Except that the constituents of the lipid are different, the method for preparing the liposome is same as that in case of the above mentioned neutral electric charge liposome.

A phospholipid such as phosphatidylcholine or sphingomyelin, cholesterol, and a positively charged higher aliphatic amine such as stearylamine were mixed together in a molar ratio of 7:2:1 or 4:1:1 to form a lipid ingredient, and FTS was enclosed in a similar manner.

(3) A negatively charged liposome enclosing FTS:

A phospholipid such as phosphatidylchlorine or sphingomyelin, cholesterol, an a negatively charged higher aliphatic ester such as dicetyl phosphate or sulfatide were mixed together in a molar ratio of 7:2:1 or 4:1:1 to form a lipid ingredient, and FTS was enclosed in a similar manner.

Example 5 An ointment

In purified water was dissolved 2 mg of $FTS.CH_3COOH.2H_2O$ (prepared by Mitsui Seiyaku Kogyo K K). Next, 25 g of white vaseline, 20 g of stearyl alcohol, 4 g of HCO-60 and 1 g of glycerol monostearate were weighed and mixed. A previously prepared aqueous solution (containing FTS) of 12 g of propylene glycol, 0.1 g of methyl p-hydroxybenzoate and 0.1 g of propyl p-hydroxybenzoate was added to the mixture and the whole was thoroughly blended to form an emulsion which was then mixed until it was cooled and solidified.

Example 6 A suppository

In a hard fat previously warmed was dispersed 10 mg of $FTS.CH_3COOH.2H_2O$ (prepared by Mitsui Seiyaku Kogyo K K). The total amount was adjusted to 2 g.

Example 7 A capsule for nasal use

In 29.95 mg of miglyol 812 neutral oil (Dynamite Nobel Co.) was dissolved under a sterilizing condition 0.05 mg of FTS. This solution was charged into a conventional unit-dose capsule which was treated with an applying device just before use.

Example 8 Nasal drops

In distilled water were dissolved at room temperature sodium dihydrogen phosphate, disodium hydrogen phosphate, sodium chloride and EDTA-disodium salt in amounts shown below. FTS was dissolved in this solution which was then filtered through a membrane filter.

| | |
|---|---|
| FTS | 0.10 mg |
| Sodium monohydrogen phosphate $2H_2O$ | 0.30 mg |
| Sodium dihydrogen phosphate $12H_2O$ | 10.10 mg |
| Benzalconium chloride | 0.10 mg |
| Ethylenediamine tetraacetic acid disodium salt (EDTA) | 0.50 mg |
| Sodium chloride | 4.50 mg |
| Distilled water | 987.60 mg |
| pH value | 5.0 ± 0.3 |

Example 9 A nasal spray preparation

In hydroxypropylcellulose or hydroxypropylmethylcellulose was suspended $FTS.CH_3COOH.2H_2O$ (prepared by Mitsui Seiyaku Kogyo K K). The suspension was processed to a spray preparation by the aid of a spray-preparing machine.

Given below are examples for pharmacological experiments and Toxicity experiments concerning the medicament of this invention.

EXPERIMENTAL EXAMPLE 1

Effects of a single administration of FTS on diabetes rats

Male Wister rats (body weight: 180–220 g) were injected, after fasting for 24 hours, intraperitoneally with pentobarbital sodium and then anesthetized. The rats were intravenously injected at tail vein with Alloxan dissolved in a 0.1M phosphate buffer solution (pH 7.4) in a dose of 75 mg/kg of 15 mg/rat or with STZ dissolved in a 0.1M sodium citrate buffer solution (pH 4.5) in a dose of 75 mg/kg or 15 mg/rat. Simultaneously, the rats were intravenously injected with 60 μg/kg of FTS to make a group of FTS-administered rats or with PBS to make a control group of the rats. With the lapse of time, blood was periodically extracted from the jugular vein to measure the blood sugar value and the blood plasma AG value in the acute phase of diabetes. The blood sugar value was measured with Fuji Dri Chem 2000 analyzer system (Fuji Photo Film Co.) while the AG value was measured with gas liquid chromatography (Shimazu Mfg. Co.). A result of the measurements is shown in the following Tables 1, 2 and 3.

EXPERIMENTAL EXAMPLE 2

Effects of a repetitive administration of FTS on diabetes rats

Male Wister rats (body weight 250 g) were treated as described in Experimental Example 1 and injected intravenously as tail vein with 20 mg of Alloxan. Simultaneously, the rats were intravenously injected with FTS 15 μg/0.3 ml PBS/III for the FTS-administered group and with PBS for a control group. After 20 hours and 44 hours, the rats of the FTS-administered group were subcutaneously injected with FTS 20 μg/0.1 ml PBS/III while the rats of the control groups were subcutaneously injected with PBS. After 71 hours, the rats were sacrificed and the blood sugar value and the blood plasma AG value in the sub-acute phase of diabetes were measured. A result of the measurements is shown in Table 4.

EXPERIMENTAL EXAMPLE 3

Effects of a long-term administration of FTS on BB rats

BB rats were bred in a clean room and the rats were classified into a control group consisting of 2 male rats and 5 female rats and a group of FTS-administration consisting of 2 male rats and 5 female rats. From 5 weeks old, the rats in the group of FTS-administration and the rats in the control group were intraperitoneally injected once a week with 100 μg/0.3 ml PBS/rat and with PBS, respectively, and the body weight of the rats was measured once a week. The urine sugar of each rat was periodically checked, and rats reduced in body weight or weakened were sacrificed at that stage whereupon BS, the number of leucocytes, and lumphocyte subset were measured and a histropathological examination of pancreas was also carried out. A result of the experiment is shown in Table 5 and FIG. 1.

EXPERIMENTAL EXAMPLE 4

Toxicity test

No toxicity was observed when 50 mg/kg and 100 mg/kg of FTS as the effective ingredient were subcutaneously administered for consecutive 14 days to a group of five ddy male mice of 5 weeks old.

EXPERIMENTAL EXAMPLE 5

Toxicity Test

No toxicity was observed when 30 mg/kg of FTS as the effective ingredient wa subcutaneously administered for consecutive 21 days to a group of ten Wister rats of 5 weeks old.

TABLE 2

Effects of a single administration of FTS on STZ-induced diabetes rats

Glucose in blood (mg/dl) Average value

Time (hr) after simultaneous administration of STZ (75 mg/kg) and a given dose of FTS)

| | 0 | 1 | 2 | 3 | 4 | 5 | 6 | 7 |
|---|---|---|---|---|---|---|---|---|
| STZ alone (control group) | 101 | 221 | 373 | 527 | 635 | 662 | 652 | 457 |
| STZ + FTS 15 μg | 91 | — | 288 | — | 436 | 510 | 482 | 403 |
| STZ + FTS 50 μg | 90 | — | 232 | 358 | — | 408 | 390 | 362 |
| STZ + FTS 250 μg | 95 | — | 340 | 557 | 619 | 604 | 591 | 471 |

An average value in 2-5 experiments in case of using 3 rats/group
—: No experiment

TABLE 3

Total excretion amount of glucose in urine (US) and AG value (AG) in blood plasma of diabetes rats to which FTS was administered (Average Value ± SD)

| Treatment | Rats used | US (mg) | AG (μg) |
|---|---|---|---|
| Physiological aline | 3 | ND | 9.7 |
| FTS 25 μg | 3 | ND | 10.1 |
| Alloxan 15 mg/rat + FTS 15 μg (60 μg/kg) | 5 | 21 ± 19 | 8.3 ± 1.7 |
| Alloxan 15 mg/rat + FTS 25 μg | 3 | 86 | 6.4 |
| Alloxan 15 mg/rat + FTS 250 μg | 4 | 72 | 7.1 |
| Alloxan 15 mg/rat alone | 35 | 147 + 21 | 1.9 × 0.2 |
| STZ 15 mg/rat + FTS 15 μg | 2 | 106 | 3.0 |
| STZ 15 mg/rat + FTS 25 μg | 5 | 93 | 3.7 |
| STZ 15 mg/rat + FTS 50 μg (200 μg/kg) | 6 | 87 ± 29 | 4.2 ± 1.9 |
| STZ 15 mg/rat + FTS 100 μg | 3 | 141 | 1.6 |
| STZ 15 mg/rat + FTS 250 μg | 4 | 129 | 2.5 |
| STZ 15 mg/rat alone | 46 | 153 ± 16 | 2.1 ± 0.2 |

TABLE 1

Effects of a single administration of FTS on Alloxan-induced diabetes rats

Glucose in blood (mg/dl) Average value ± S.D.

Time after simultaneous administration of Alloxan (75 mg/kg) + FTS 15 μg (hr)

| | 0 | 0.5 | 1 | 2 | 3 | 4 | 5 | 6 | 7 |
|---|---|---|---|---|---|---|---|---|---|
| Alloxan alone* | 111 ± 18 | 372 ± 117 | 447 ± 168 | 480 ± 123 | 502 ± 129 | 533 ± 80 | 581 ± 59 | 644 ± 65 | 641 ± 99 |
| Alloxan + FTS | 97 ± 14 | 144 ± 135 | 183 ± 190 | — | 212 ± 190 | — | 189 ± 183 | — | 241 ± 141 |
| FTS | 101 ± 22 | 109 ± 38 | 125 ± 49 | — | 123 ± 53 | — | 148 ± 47 | — | 164 ± 59 |

*Control group
Remarks: An average value in 2-5 experiments in case of using 3 rats/group
—: No experiment

TABLE 4

Effects of repetitive administration of FTS on Alloxan-induced diabetes rats

|  | Blood sugar (BS) value and AG value in blood plasma (average value ± SD) | |
|---|---|---|
|  | BS (mg/dl) | AG (μg/dl) |
| Control group (8 rats) | 500 + 138 | 0.06 + 0.03 |
| FTS-administered group (9 rats) | 324 + 125* | 2.17 + 3.21* |

*: $p < 0.05$

TABLE 5

Lymphocyte subset of BB rats

|  | OX-19 lymphocyte subset (%) | |
|---|---|---|
|  | Control group (6 rats) | FTS-administered group (5 rats) |
| Peripheral blood | 8.1 ± 3.3 | 3.7 ± 2.4* |
| Spleen | 16.2 ± 3.6 | 7.7 ± 1.3** |

**: $p < 0.01$,
*: $p < 0.05$

As described above, the medicament concerned with the present invention is epoch-making in that the effect of prevention and remedy of the above mentioned diseases which has not yet been obtained by conventional medicaments can be achieved by activation of immunity or living body-protecting system and the like. Especially in case of diabetes, FTS shows an inhibitory effect to high blood sugar in subacute or acute phase not only in repetitive administration but in a single administration to a drug-induced diabetes rats. Further, FTS shows suppression of the occurrence of symptoms or transition to a mild case also in naturally attacked diabetes animals. It has thus been made clear that FTS suppresses progress of diabetes in initial stage and inhibits injury or destroy of Langelhans island of pancreas (inhibition of IDDM). Accordingly, the present invention provides an epoch-making therapeutic method in that labor and pain can be eliminated from the patients compelled to receive insulin injection over their life span due to destroy of Langelhans island and that troublesome examinations and alimentotherapy can be omitted.

Even if a person has been attacked by diabetes, administration of the medicament of this invention enable to maintain the symptom of slight destroy of Langelhans island, thus arresting diabetes to a serious state. Unlike the conventional allopathic treatment with a conventional oral anti-diabetes drug or insulin, development of a method for complete remedy of diabetes is expected by administration of the medicament concerned with the present invention. It can also be expected that the administration of the medicament of this invention can arrest diabetes to prevent disorder of nervous system, ablepsia, myocardial infraction, cerebral apoploxy and renal disorder complicated with diabetes. Further, the medicament of this invention is useful for the remedy of disorders of extrapancreatic secretory system such as acute pancreatitis and chronic pancreatitis, and can alleviate various symptoms in case of Langelhans island being destroyed to reduce excretion of insulin and cause diabetes. The nonapeptide (FTS) used in the medicament of this invention is a peptide originating from animals and is a natural substance. Accordingly, it is quite non-toxic in living body and has no problem of anti-genicity or anaphylactic shock, unlike the case of FTS analogs having a similar amino acid configuration.

Thus, the medicament concerned with the present invention can be used as safe and useful medical preparations and veterinary medical preparations.

Figure 1:
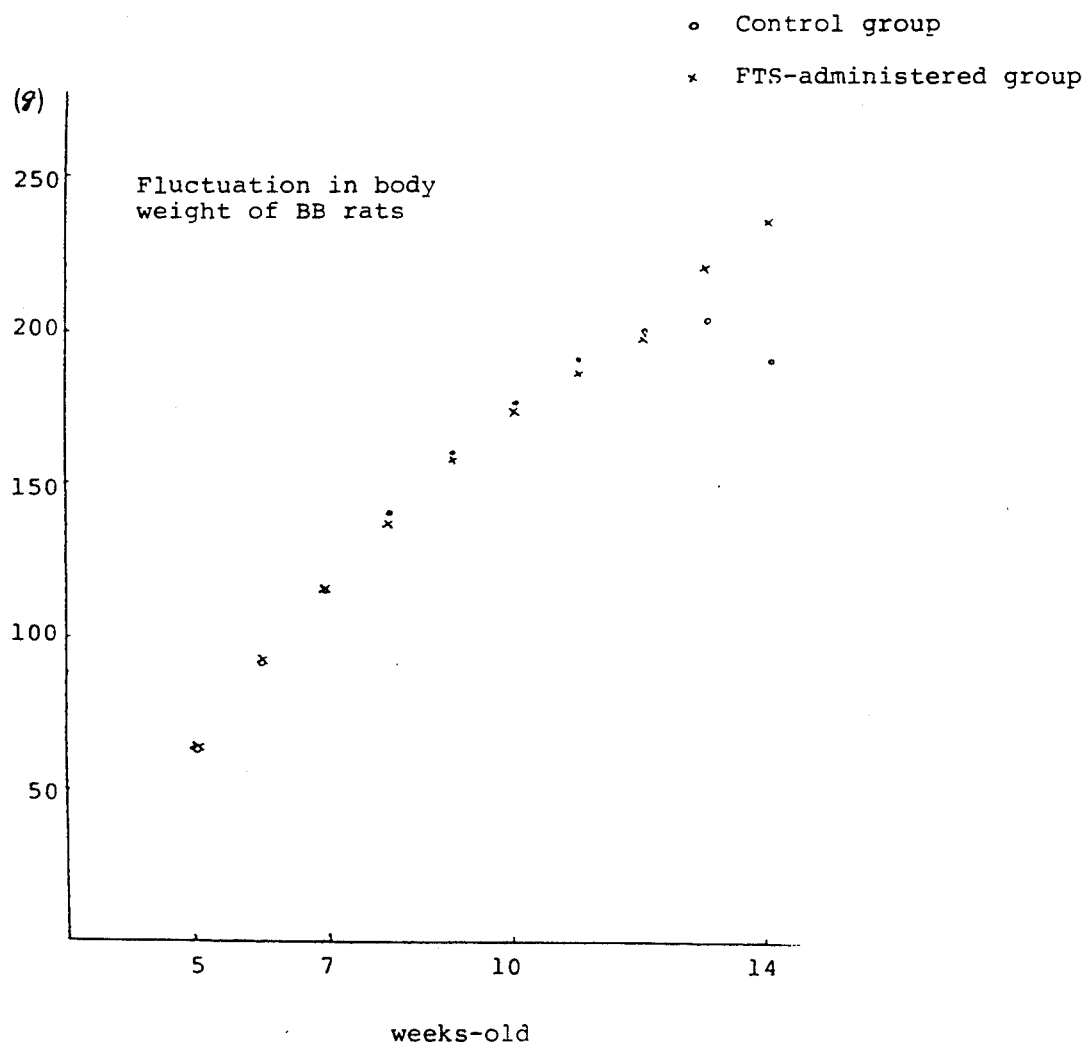
FIG. 1 is a graph showing a result of one example of pharmacological experiments (Experimental Example 3) showing the effect of the medicament of this invention.

We claim:

1. A method of treating diabetes consisting essentially of administering to a patient having same an effective amount of a nonapeptide consisting essentially of amino acids in the L form and having the following configuration:

pGlu-Ala-Lys-Ser-Gln-Gly-Gly-Ser-Asn or an ester and amide at the carboxyl group of the C-terminal of the asparagine, or a pharmacologically acceptable ammonium salt thereof or a salt with an organic base.

2. The method of claim 1, wherein the nonapeptide is administered in an amount of from 0.1 μg to 500 mg/day per kilogram of the patient's body weight in single or divided doses.

3. The method of claim 1, wherein the nonapeptide is encapsulated in a phospholipid and administered to the patient as a liposome.

4. A method of treating acute pancreatitis comprising administering to a patient having same an effective amount of a nonapeptide composed of amino acids in that L form and having the following configuration:

pGlu-Ala-Lys-Ser-Gln-Gly-Gly-Ser-Asn or an ester and amide at the carboxyl group of the C-terminal of the asparagine, or a pharmacologically acceptable alkali metal, alkaline earth metal salt thereof or a salt with an organic base.

5. The method of claim 4, wherein the nonapeptide is administered in an amount of from 0.1 μg to 500 mg/day per kilogram of the patient's body weight in single or multiple doses.

6. The method of claim 5, wherein the nonapeptide is encapsulated in a phospholipid and administered to the patient as a liposome.

* * * * *